United States Patent [19]

Sugiura

[11] Patent Number: 4,602,213

[45] Date of Patent: Jul. 22, 1986

[54] AUTOMATIC TUNING CIRCUIT FOR NUCLEAR MAGNETIC RESONANCE APPARATUS

[75] Inventor: Satoshi Sugiura, Tochigi, Japan

[73] Assignee: Tokyo Shibaura Denki Kabushiki Kaisha, Kawasaki, Japan

[21] Appl. No.: 565,539

[22] Filed: Dec. 27, 1983

[30] Foreign Application Priority Data

Dec. 28, 1982 [JP] Japan .............................. 57-233506
Dec. 28, 1982 [JP] Japan .............................. 57-233515

[51] Int. Cl.[4] ............................................. G01R 33/20
[52] U.S. Cl. ................................... 324/307; 324/313
[58] Field of Search ................ 324/300, 307, 313, 314

[56] References Cited

U.S. PATENT DOCUMENTS

| | | | |
|---|---|---|---|
| 3,140,440 | 7/1964 | Senstad | 324/314 |
| 3,388,322 | 6/1968 | Anderson et al. | 324/310 |
| 4,110,681 | 8/1978 | Hofer et al. | 324/313 |
| 4,171,511 | 10/1979 | Hill | 324/313 |

FOREIGN PATENT DOCUMENTS 1023809 3/1966 United Kingdom .
1167282 10/1969 United Kingdom .

Primary Examiner—Michael J. Tokar
Attorney, Agent, or Firm—Finnegan, Henderson, Farabow, Garrett & Dunner

[57] ABSTRACT

In an NMR diagnostic apparatus, it is generally necessary to tune a receiver tuning unit with respect to a patient. The NMR diagnostic apparatus is comprised of a standard signal generator for generating a CW signal, a receiver tuning unit which is mainly constructed by a receiver probe head and a series circuit of a capacitor and a variable capacitance diode and receives the NMR signals induced from the CW signal, quadrature detectors which detect the NMR signals, and a signal processor which processes the detected NMR signals so as to produce the control voltages "Vc". The automatic tuning operation is carried out in such a manner that varying the control voltage "Vc" which is applied to the variable capacitance diode enables the receiver tuning unit to be tuned with respect to the object that is positioned in the receiver probe head.

16 Claims, 13 Drawing Figures

AUTOMATIC TUNING CIRCUIT FOR NUCLEAR MAGNETIC RESONANCE APPARATUS

BACKGROUND OF THE INVENTION

1. Field of the Invention

The present invention relates to a nuclear magnetic resonance diagnostic apparatus (to be referred to as an "NMR diagnostic apparatus" hereinafter) which utilizes the magnetic resonance phenomenon so as to noninvasively measure information as to the spin density and the relaxation time of a specific atomic nucleus or proton within a selected sectional slice plane of an object to be examined, e.g., a patient, for which tomographic imahe is taken, and to display information for medical diagnosis in the form of tomographic images. The invention relates, more particularly to automatic tuning circuits for the NMR diagnostic apparatus.

2. Description of the Prior Art

The NMR diagnostic apparatus as mentioned in the preamble is known from, e.g., U.S. Pat. No. 4,254,778 issued on Mar. 10, 1981.

In general, a reception section in the known NMR diagnostic apparatus, which receives NMR signals including not only FID signals but also echo pulse signals, is comprised of saddle-shaped coils, so-called "probe head coil", and an internal capacitor which constitute a resonant circuit for a receiver circuit. The NMR signals are excited by the NMR phenomenon from an object, e.g., a patient around which the probe head coil is arranged. Generally speaking, since those NMR signals are very weak in the electromagnetic field strength, it is necessarily required such a resonant circuit having an extremely high "quality factor (Q)" so as to pick up the NMR signals in a high efficiency. As a result, the resonant characteristic curve of the above-mentioned resonant circuit is very sharp. Accordingly based upon a very small variation in the capacitance component of the resonant circuit, amplitudes of the received NMR signals are greatly changed. In other words, the sensitivity of the receiver varies considerably. Meanwhile there exists a stray capacitance between the patient and the probe head coil, which is different from respective patient himself, and from respective body portion for diagnosis purposes. Consequently it is necessary to take such a diagnostic preparation in the individual patient that the capacitance of the internal capacitor is varied so as to tune to each resonant frequency the resonant circuit to which the individual patient is arranged.

It is therefore an object of the present invention to provide an NMR diagnostic apparatus having an automatic tuning circuit by which in advance of an NMR signal acquisition for diagnosis purposes, the signal reception unit can be automatically tuned.

SUMMARY OF THE INVENTION

The object of the present invention may be accomplished by providing an NMR diagnostic apparatus comprising means for applying uniformly to the object a static magnetic field; means for generating a signal which is used, on one hand, as exciting pulses and, on the other hand, as a reference signal; signal transmitter means through which the exciting pulses are applied so as to excite an imaginarily cross-sectionally sliced portion of the object to produce NMR signals therefrom; signal receiver means through which the NMR signals are received from the excited sliced portion; means for quadrature-detecting the NMR signals which are received by the signal receiver means based upon the reference signal; a control signal generation unit for generating control signals, values of which are variable, and for receiving the detected NMR signals so as to temporarily store peak values of the detected NMR signals which are derived during an application of the exciting pulses to the object; and a receiver tuning unit which is interposed between the receiver means and the detection means, and is comprised of at least a parallel resonant circuit having a variable capacitance device in conjunction with the receiver means, a resonant frequency of which is variable under the control of the control signals, whereby an automatic tuning operation is performed by applying to the variable capacitance device a given control voltage corresponding to a maximum peak value of the detected NMR signals which is selected from the peak values of the detected NMR signals temporarily stored in the control signal generation unit.

Further, the object of the present invention may be accomplished by providing an NMR diagnostic apparatus comprising means for applying uniformly to the object a static magnetic field; means for generating a continuous wave signal which is used, on one hand, as exciting pulses and, on the other hand, as a tuning signal; signal transmitter means through which the exciting pulses are applied so as to excite an imaginarily cross-sectionally sliced portion of the object to produce NMR signals therefrom; signal receiver means through which the NMR signals are received from the excited sliced portion and independently the tuning signal is applied to the object; means for envelope-detecting the tuning signal so as to produce a DC tuning signal having an amplitude proportional to that of the tuning signal; a control signal generation unit for generating control signals, values of which are variable, and receiving the detected DC turning signals so as to temporarily store values of the DC tuning signals at a given instant which are derived during an application of the tuning signals to the object; and a receiver tuning unit which is interposed between the receiver means and the detection means, and is comprised of at least a parallel resonant circuit having a variable capacitance device in conjunction with the receiver means, a resonant frequency of which is variable under the control of the control signals, whereby an automatic tuning operation is performed by applying to a variable capacitance device a given control voltage corresponding to a maximum value of the detected DC tuning signal which is selected from the values of the detected DC tuning signals temporarily stored in the control signal generation unit.

Moreover, the object and the feature of the present invention may be realized by providing an NMR diagnostic apparatus comprising for generating a continuous wave signal which is used, on one hand, as exciting pulses and, on the other hand, as a tuning signal; signal transmitter means through which the exciting pulses are applied so as to excite an imaginarily cross-sectionally sliced portion of the object to produce NMR signals therefrom, and the tuning signal is independently applied to the sliced portion of the object; signal receiver means through which the NMR signals are received from the excited sliced portion and the tuning signal induced from the same is independently received; means for envelope-detecting the tuning signal so as to produce a DC tuning signal having an amplitude proportional to that of the tuning signal; a control signal generation unit for generating control signals, values of which are variable, and receiving the detected DC tuning signals so as to temporarily store values of the DC tuning signals at a given instant which are derived during an application of the tuning signals to the object; and a receiver tuning unit which is interposed between the receiver means and the detection means, and is comprised of at least a parallel resonant circuit having a variable capacitance device in conjunction with the receiver means, a resonant frequency of which is variable under the control of the control signals, whereby an automatic tuning operation is performed by applying to a variable capacitance device a given control voltage corresponding to a maximum value of the detected DC tuning signal which is selected from the values of the detected DC tuning signals temporarily stored in the control signal generation unit.

BRIEF DESCRIPTION OF THE DRAWINGS

For a better understanding of these and other objects of the present invention, reference is had to the following detailed description of the invention to be read in conjunction with the following drawings, wherein.

DETAILED DESCRIPTION OF THE PREFERRED EMBODIMENTS

The preferred embodiments of the present invention will now be described.

According to one technical idea, upon receipt of the NMR signals through the probe head coil, i.e., the receiver coil from the object, the NMR signals are detected in the quadrature detector. Accordingly a desirable control voltage for the controllable capacitance device such as the variable capacitance diode is obtained by processing the quadrature-detected NMR signals so as to automatically tune the signal reception circuit to the object.

On the other hand, according to the other technical idea, continuous wave (CW) signals such as sinesoidal signals generated from the standard signal generator are applied to the signal reception circuit having the parallel resonant circuit. Those CW signals applied to the signal reception circuit are detected in the envelope detector. A desirable control voltage for the controllable capacitance device is obtained by processing the envelope-detected CW signals so as to automatically tune the signal reception circuit to the object. In other words, not the NMR signals, but the CW signals are utilized to determine the control voltage in this technical idea.

The following embodiments belong to the first technical idea of the present invention as described just before.

Figure 1:
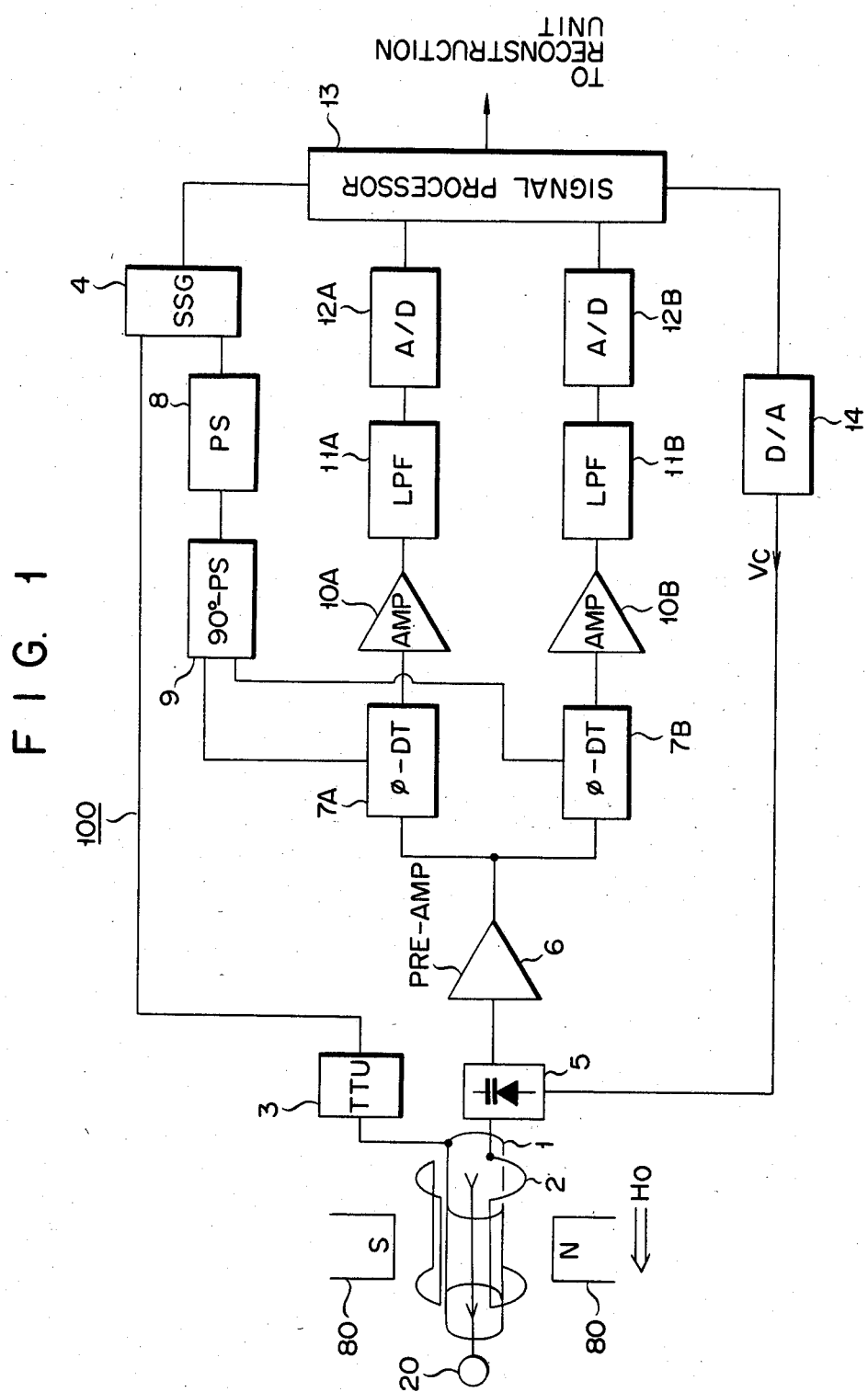
FIG. 1 shows a block diagram of an NMR diagnostic apparatus belonging to a first technical idea according to one preferred embodiment.

FIG. 1 shows a block of an NMR diagnostic apparatus according to one preferred embodiment.

It should be noted that for convenience and clarity of illustration, the known reconstruction circuit and the display device for the computerized tomographic images are omitted from the drawing, which are necessary for the NMR diagnostic apparatus.

Referring to FIG. 1, the NMR diagnostic apparatus 100 is comprised of the following components. A pair of electromagnets 80 is provided in a given position to apply a static magnetic field Ho to an object 20. Other electromagnets for applying gradient magnetic field are omitted for the simplicity of illustration. Reference numeral 1 denotes a transmitter coil which constitutes a transmitter probe head. Reference numeral 2 indicates a receiver coil which constitutes a receiver probe head. Those transmitter/receiver probe heads 1, 2 constitute a crossed coil type probe head in which the saddle-shaped transmitter/receiver coils are positioned in such a manner that the transverse axis of the transmitter coil 1 intersects that of the receiver coil 2 at a right angle.

A transmitter tuning unit 3 is tuned to a specific radio frequency of the RF signals generated by the standard signal generator 4 and RF exciting pulse signals which are tuned to the specific atomic nucleus in the object 20 positioned in the transmitter/receiver coils 1 and 2, are applied to the object 20 via the transmitter probe head 1. On the other hand, the NMR signals excited in the object 20 are received via the receiver probe head 2 to a receiver tuning unit 5, and then amplified by a preamplifier 6, thereafter applied to two phase detectors 7A, 7B, i.e., quadrature detectors. To the phase detectors 7A, 7B, the signals which have been generated by the standard signal generator 4, and phase-shifted in a phase shifter 8 and a 90°-phase shifter 9 respectively, are applied as reference signals which have the same frequency as the NMR signals, and phases of which are different from each other. The NMR signals which have been phase-detected in the phase detectors 7A and 7B, are amplified in amplifiers 10A, 10B respectively, analog-to-digital converted in A/D converters 12A, 12B, and applied into a signal processor 13 as the digital NMR signals. This signal processor 13 produces echo signal data by performing a given phase correction processing by use of the digital NMR signals, and also produces a control voltage "Vc" (will be described later). A D/A converter 14 which is connected between the signal processor 13 and the last-mentioned function part of the signal processor 13, constitutes a control signal generation unit and this unit generates the control voltage "Vc" for a controllable capacitance device in response to the detected NMR signals. The control voltage "Vc" is to be applied to the receiver tuning unit 5.

Figure 2:
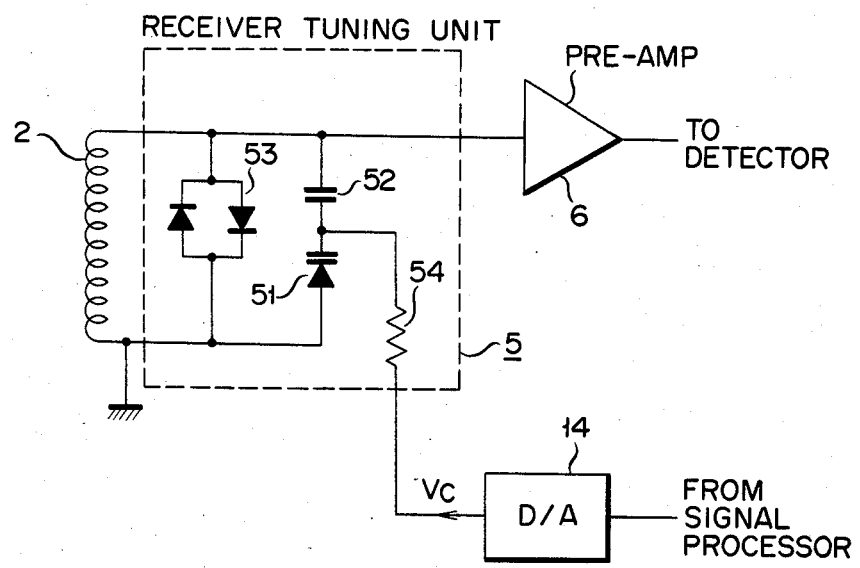
FIG. 2 shows a circuit diagram of a first embodiment of the receiver turning unit shown in FIG. 1.

FIG. 2 shows one embodiment of the receiver tuning unit 5 in the circuit diagram shown in FIG. 1.

Referring to FIG. 2, a controllable capacitance device, e.g., a variable capacitance diode 51 and a capacitor 52 which is series-connected to the cathode of the diode 51 constitute a series circuit arrangement. The variable capacitance diode 51 may change its capacitance in response to the reverse biasing voltage. The capacitor 52 has a large capacitance. The series circuit arrangement is connected in parallel to the receiver coil 2 so as to constitute an LC parallel resonant circuit. This LC parallel resonant circuit is designed such that the capacitance of the capacitor 52 is considerably greater than that of the variable capacitance diode 51, so that a total series capacitance can be practically determined only by the capacitance of the variable capacitance diode 51. That is, supposing that the capacitance of the variable capacitance diode 51 is indicated as "C51" and that of the capacitor 52 is as "C52", the total series capacitance "$C_T$" is calculated by the following equation (1) under the condition of C52>>C51.

$$C_T = \frac{C51 \cdot C52}{C51 + C52} \quad (1)$$

$$\approx \frac{C51 \cdot C52}{C52}$$

$$\approx C51$$

It should be noted that in the circuit diagram shown in FIG. 2 the anode of the variable capacitance diode 51 is grounded, but the capacitor 52 of the series circuit arrangement may be alternatively grounded.

Further to the LC parallel resonant circuit, a crossed diode 53 is connected in parallel. A junction between the variable capacitance diode 51 and the capacitor 52 is connected via a resistor 54 to the output of the D/A converter 14, so that the control voltage "Vc" can be applied to the junction through the resistor 54. As a result, the capacitance of the diode 51 can be varied in accordance with the control voltage "Vc". The resistor 54 must have a high resistance, to block high frequency NMR signals from flowing into the D/A converter 14. An NMR signal line connected to the preamplifier 6 is DC-cut from the D/A converter 14 by the capacitor 52. The functions of the crossed diode 53 are to prevent the input stage of the preamplifier 6 from being electrically destroyed due to leakage of the high power RF exciting pulses which are applied from the transmitter side 3, 4 to the object 20, and also due to distortion which is caused by the variable capacitance diode 51. The receiver tuning unit 5 is constituted by those elements, i.e., the variable capacitance diode 51, the capacitor 52, the crossed diode 53 and resistor 54.

Technical specifications of the circuit elements employed in the circuit shown in FIG. 2 will now be described.

The saddle-shaped receiver probe head coil 2 has an inductance of approximately 10 μH, the crossed diode 53 is a commercially available switching diode; type No. 1 S1585 VTP (TOSHIBA). The variable capacitance diode 51 is also a commercially available switching diode; type No. 1 SV 75 (TOSHIBA), and has a capacitance variation range between approx. 65 pF (reverse biasing voltage: 0 V) and approx. 12 pF (the voltage: −10 V). The D/A converter 14 is of a type DAC-HZ12B (DATEL INC.). When a 12-bit digital signal is input from the signal processor 13, 0 to 10 V AC signal is output. This 0 to 10 V AC voltage signal is utilized as the control voltage "Vc" for the variable capacitance diode 51. The control voltage "Vc" is applied via the resistor 54 having 100 kΩ (¼ W) to the cathode of the variable capacitance diode 51. The capacitor 52 is of a ceramic type 0.1 μF/50 V.

Then the following description is given to a method for setting the control voltage "Vc" that is required for the automatic tuning operation as a feature of the present invention.

Figure 3:
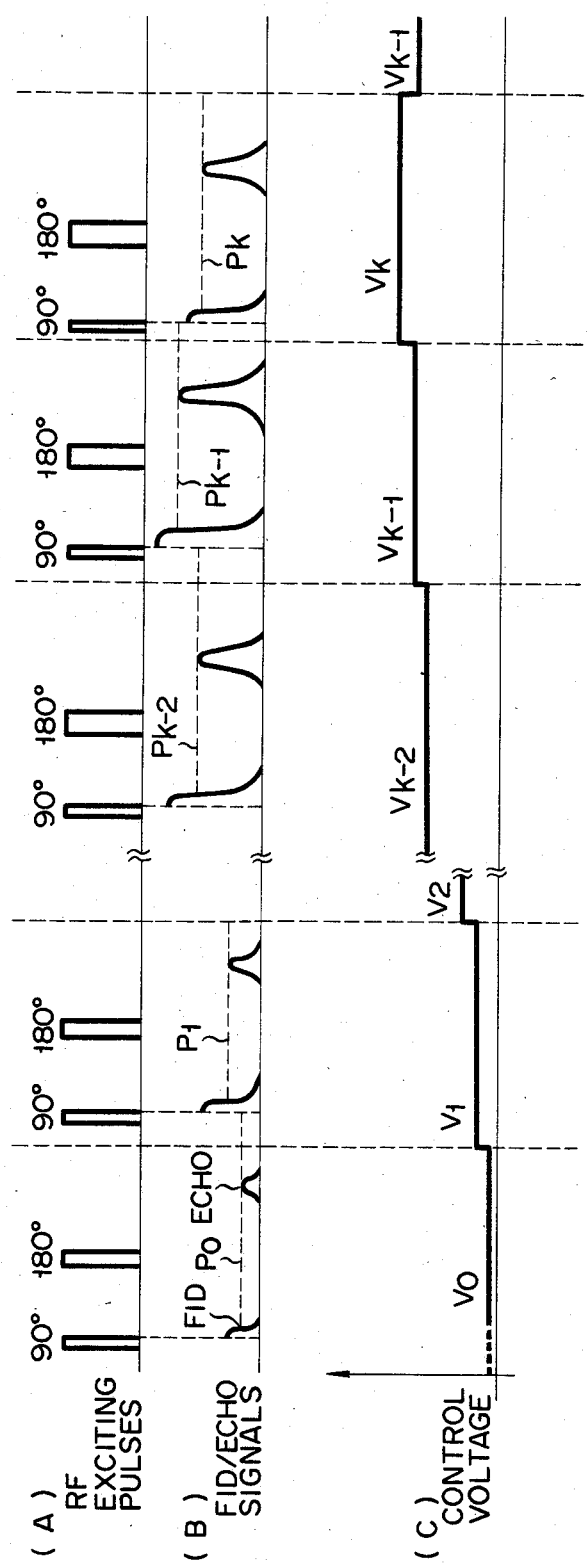
FIGS. 3A, 3B and 3C are waveform diagrams for explaining an automatic tuning unit shown in FIG. 1.

As an initial condition, RF exciting pulse series shown in FIG. 3A (90°-τ-180°, τ being a predetermined time interval) are applied through the receiver probe head 2 to the object 20 which is also inserted in the transmitter probe head 1. As previously explained, the NMR signals containing the FID signal and the echo signal are obtained by the receiver probe head 2.

First, the control voltage "Vc" derived from the D/A converter 14 has been preset to a minimum value "Vo" by adjusting the signal processor 13. Secondly, the NMR signals received by the receiver probe head 2 are processed in the preamplifier 6, the quadrature-phase detectors 7A, 7B, the low pass filters 11A/11B and the A/D converters 12A/12B to be applied to the signal processor 13 under the application of the RF exciting pulses. Consider that peak values of the echo signals which have filtered through the low pass filters 11A/11B are indicated by "$P_N$" (N=0, 1, 2, ... n) and temporarily stored in signed processor 13. For example, the first peak value is by "Po" (see the leftmost waveform in FIG. 3B).

Thirdly, echo signal acquisition is carried out by controlling an operation program of the signal processor 13 so as to set the control voltage "Vc" from the D/A converter 14 to V1=Vo+ΔV. Then at this signal collection, a peak value of the filtered echo signal is denoted by "P1" (see FIG. 3B).

Furthermore when the control voltage "Vc" is increased in such a way: V2=V1+ΔV, V3=V2+ΔV, ..., Vk=Vk−1+ΔV, ... Vn=Vn−1+ΔV, the peak value "Pn" is indicated by: P2, P3, ..., Pk, ..., Pn respectively.

Assume that a control voltage "Vc" is "$V_R$" to obtain the desirable parallel resonant condition of the receiver tuning unit 5 by changing the capacitance of the variable capacitance diode 51. If the initial control voltage "Vo" is sufficiently smaller than the desirable control voltage "$V_R$", the LC parallel resonant circuit gradually shifts its condition from the conditions apart from the resonance until the resonant condition by slightly increasing the control voltage "Vc" derived from the signal processor 13, so that the peak value "Pn" of the echo signal increases gradually until it reaches the resonant peak value "Pk−1". In other words, when a certain control voltage "Vm" is applied to the variable capacitance diode 51 (m<n), a peak value of the echo signal becomes "Pm" is smaller than the preceding peak value "Pm−1", where "m" is smaller than "n". Consequently the control voltage "Vc=Vm−1 (=$V_R$)" corresponding to the above preceding peak value "Pm−1" is a value for obtaining the LC parallel resonance. The just-explained tuning operation is described in a flow chart of FIG. 4.

The subsequent operation is to collect the NMR signals for obtaining the tomographic images. During this operation, the above-mentioned desirable control voltage "$V_R$" is being applied to the variable capacitance diode 51. Moreover, if one object is substituted by the other, the above-described tuning operation is carried out prior to the NMR signal acquisition, with the result that the tuning of the receiver tuning unit 5 can be automatically realized.

Another embodiment belonging to the first technical idea will now be described.

Figure 5:
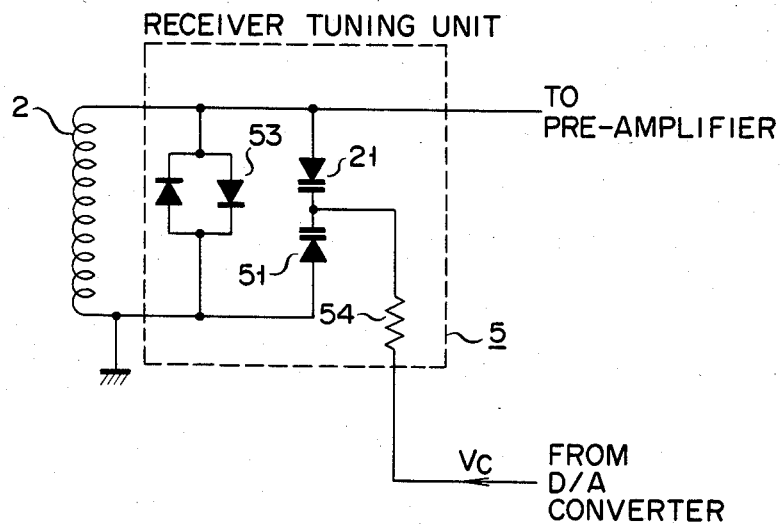
FIGS. 5 and 6 show circuit diagrams of second and third embodiments of the receiver tuning unit shown in FIG. 1.

As shown in FIG. 5, a further variable capacitance diode 21 is employed instead of the capacitor 52 shown in FIG. 2 in such a manner that the cathode of the variable capacitance diode 51 is connected to that of the other variable capacitance diode 21, a junction of which being connected via the resistor 54 to the D/A converter 14.

It is very obvious that a series connection direction of the variable capacitance diode 51 and the capacitor 52 may be reversed.

A loop type receiver coil may be alternatively employed instead of the saddle type one.

In the previous embodiment, the echo signals were obtained by applying the 180° pulse signal, and thus the adequate control voltage "$V_R$" was automatically obtained from those echo signals. However the adequate control voltage "$V_R$" may be also obtained from the FID signal.

Figure 6:
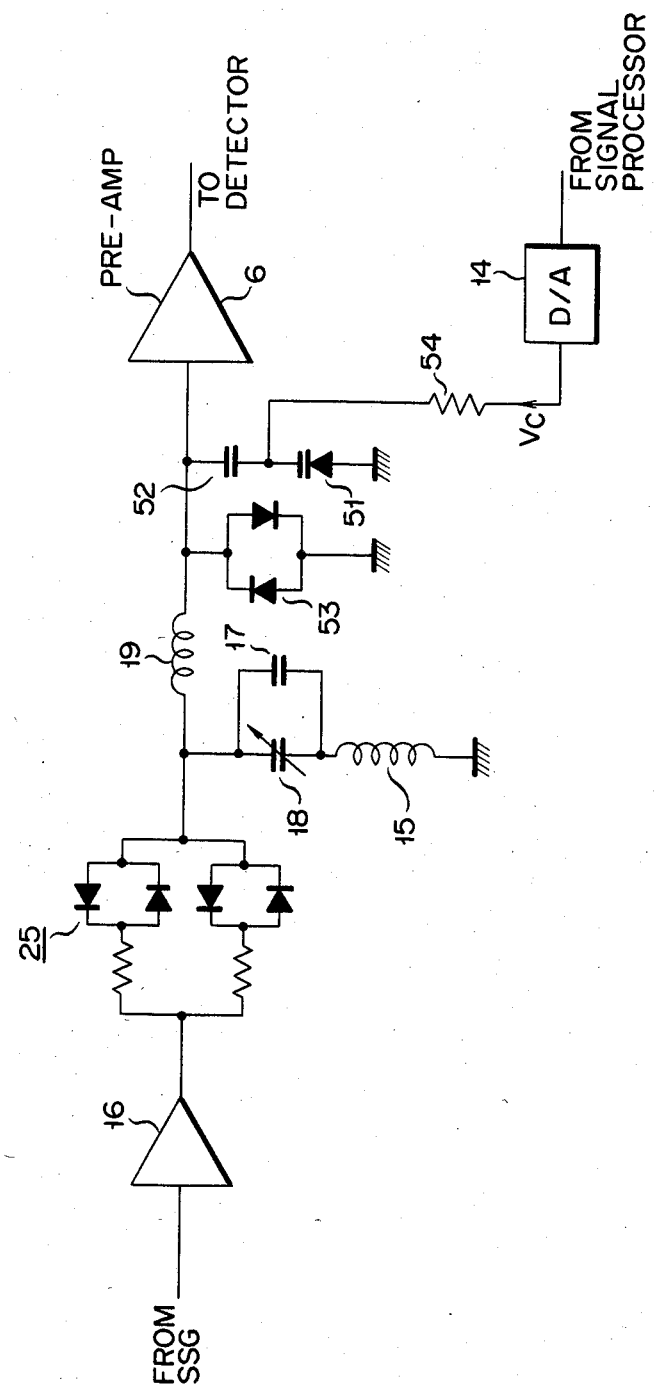

Furthermore, the crossed coil type transmitter/receiver probe head 1, 2 may be substituted by a single coil type transmitter/receiver probe head 15 as shown in FIG. 6. In a circuit diagram shown in FIG. 6, the same number is given to the similar circuit element shown in FIG. 2.

The single coil type transmitter/receiver probe head 15 is constructed by a common coil. A parallel circuit arrangement of a variable vacuum capacitor 18 (4~30 pF/21 kVp, ITT-Gennings INC.) and an RF power ceramic capacitor 17 (100 pF to 200 pF/5 kVDC) is series-connected to the transmitter/receiver probe head 15. An auxiliary coil 19 is connected between the parallel circuit arrangement and the preamplifier 6 in the receiver end.

In this embodiment, a circuit constant for the resonant circuit consisting of the common probe head 15, the auxiliary coil 19, and the capacitors 17, 18, is approximately predetermined to its resonant condition by adjusting the vacuum capacitor 18 prior to the automatic tuning operation of the control voltage "Vc". The succeeding way to obtain the desirable control voltage "$V_R$" is completely the same as in the previous embodiment. Accordingly its explanation is omitted. Reference numeral 16 denotes a transmitter power amplifier into which the RF exciting pulse signal derived from SSG 4 is introduced. Reference numeral 25 indicates a parallel circuit of another crossed diode 25 which may function as protection for the preamplifier 6. Under these circuit conditions the RF exciting pulse signal is applied to the single coil type transmitter/receiver probe head coil 15 from SSG 4 through TTU 3, the transmitter power amplifier 16, crossed diode 25 and the variable vacuum capacitor 18.

As previously described in detail, there are advantages according to the first technical idea that since a control for the automatic tuning operation is directly effected based upon the NMR signals derived from the object to be examined, no extra signal supply path for the tuning control voltage "Vc" is required, and moreover the NMR signals which are necessary for diagnosis purposes can be always obtained under the optimum tuning condition between the object and the probe head.

Then the second technical idea will now be described with reference to another embodiments.

Figure 7:
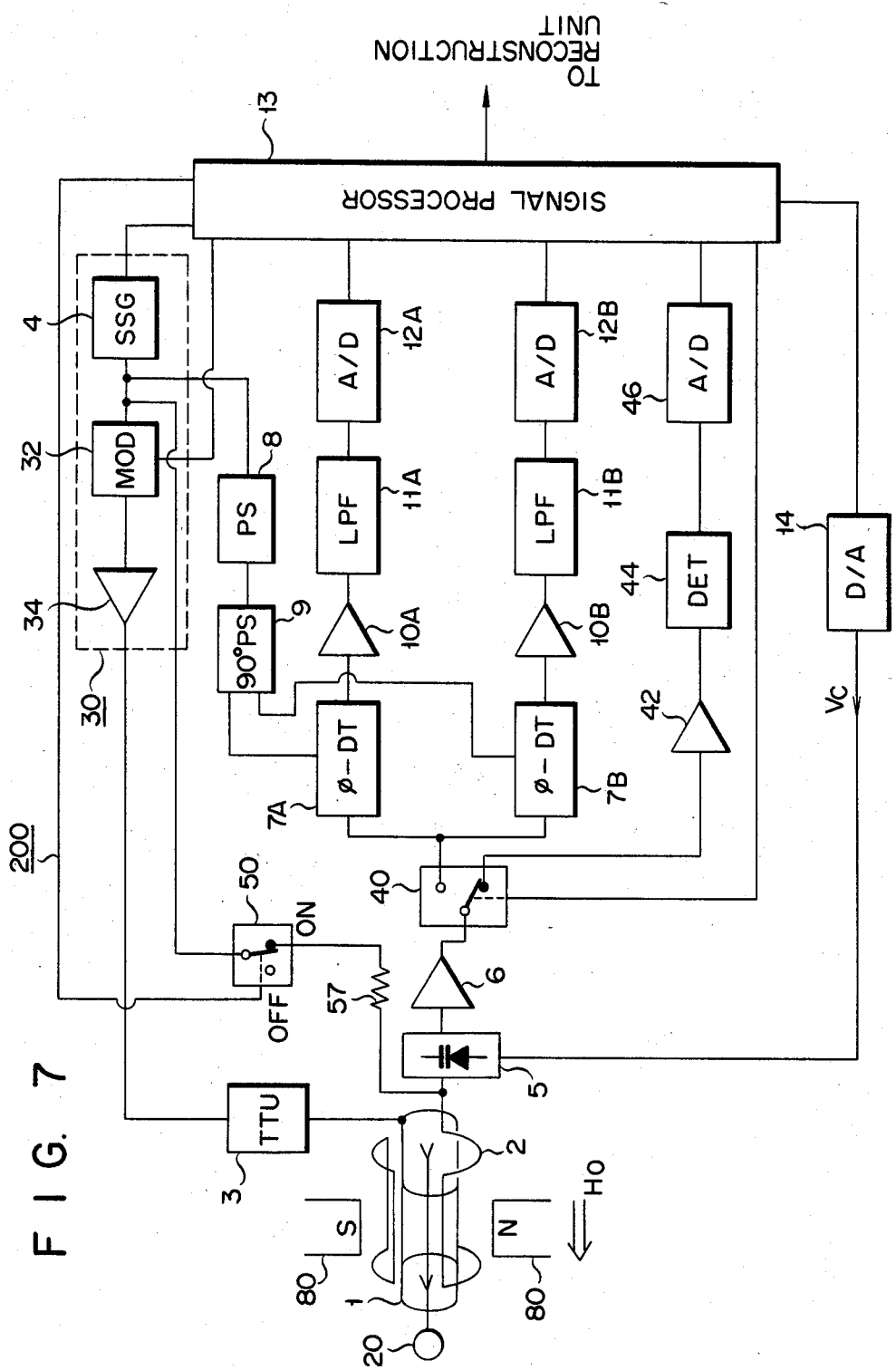
FIG. 7 shows a block diagram of one preferred embodiment belonging to a second technical idea according to the invention.

FIG. 7 shows an entire system of a first embodiment belonging to this second technical idea. An NMR diagnostic apparatus (200) shown in FIG. 7 is constructed as follows (the same numeral used in FIG. 1 is given to a similar circuit element in FIG. 7).

A transmitter unit 30 is comprised of SSG 4, a modulator 32 and a power amplifier 34. SSG 4 produces a continuous wave signal (referred to as "CW" signal) having the resonant frequency, e.g., 4.258 MHz, the modulator 32 modulates this CW signal by a given modulating signal e.g., SINC pulse signal so as to produce the RF exciting pulse, and the power amplifier 34 amplifies this RF exciting pulse by a given amplification.

On the other hand, the normal NMR signals for diagnosis purposes are received through the receiver probe head 2 to the receiver tuning unit 5, and they are amplified in the preamplifier 6, and then are applied via a selector switch 40 to two phase detectors 7A and 7B. It should be noted that a contact position of the switch 40 has been changed to the upper position (the present contact position shown in the drawing is the lower position). Two reference signals are applied to those two phase detectors 7A and 7B. Those reference signals have the same frequency as that of the NMR signals, and different phases from each other, as the CW signal generated from SSG 4 in the transmitter unit 30 is applied to a phase shifter 8 as well as a 90°-phase shifter 9 so as to be phase-shifted by 90 degrees. Then the quadrature detection is carried out by the above-described two phase detectors 7A and 7B. Thus quadrature-detected NMR signals are amplified in respective amplifiers 10A and 10B, filtered in low pass filters 11A and 11B, and then converted into corresponding digital NMR signals in A/D converters 12A and 12B respectively. The digital NMR signals are supplied to the signal processor 13 in which those signals, i.e., the cos signal component and the sin signal component are processed by a given phase correction so as to derive the echo signal data. This echo signal data is applied to the reconstruction unit (not shown) in which the tomographic information can be produced based upon the echo signal data.

While the normal NMR signal process has been described for the diagnostic purposes, the automatic tuning operation according to the second technical idea will now follow.

As previously explained, the CW signal, instead of the NMR signals as utilized in the previous technical idea, is applied to the receiver probe head coil 2 so as to obtain the optimum control voltage "$V_R$".

A circuit arrangement for the automatic tuning operation is constructed as follows. The CW signal is being applied to the receiver probe head 2 prior to the NMR diagnosis. The received CW signal from the receiver tuning unit 5 is supplied to an envelope detector 44 through the preamplifier 6, the switch 40 and an amplifier 42. Accordingly the CW signal is envelope-detected and thereafter converted into corresponding digital signal. This digital signal is processed in the signal processor 13 so as to obtain the control voltage "Vc" (a detailed description of which will be given later). The control voltage "Vc" is converted into analog voltage signal by the D/A converter 14, and then applied to the variable capacitance device of the receiver tuning unit 5.

A selector switch 50 is controlled in such a manner that when the CW signal is applied to the receiver probe head 2, it is changed to the "ON" position, and when the RF exciting pulse signals are applied to the transmitter probe head 1, it is changed to the "OFF"

position. This control is effected by the signal processor 13.

Figure 8:
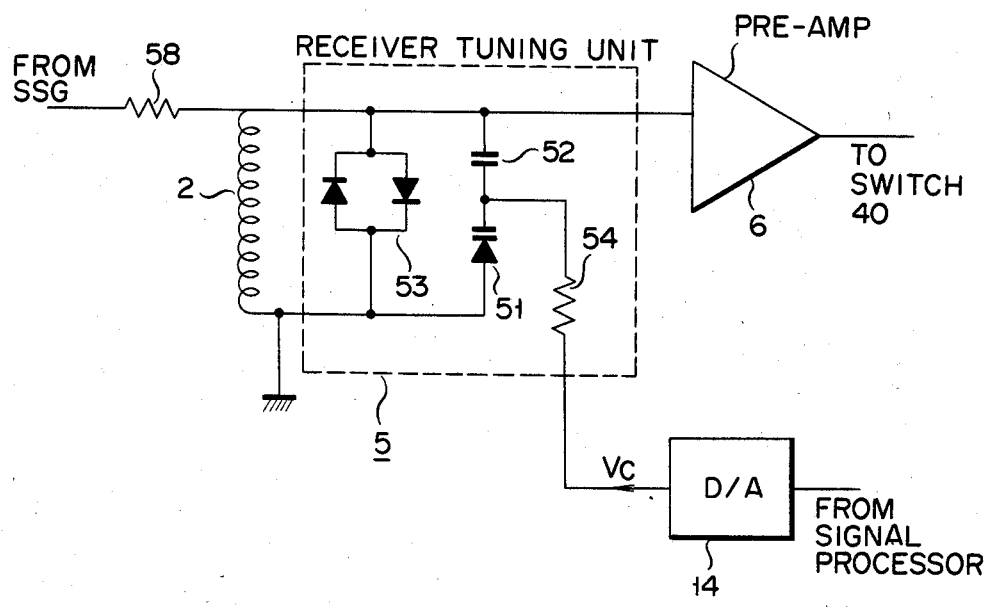
FIG. 8 is a circuit diagram of a first embodiment of the receiver tuning unit shown in FIG. 7.

FIG. 8 shows a detailed circuit diagram of the receiver tuning unit 5 and also its peripheral circuit. As readily understood from FIG. 8, a circuit construction of the drawing is substantially same as in FIG. 2. An explanation on the same circuit will be therefore omitted.

A resistor 54 has a higher resistance value so as to prevent leakage of the high frequency NMR signals into the D/A converter 14, a signal line to the preamplifier 6 is DC-decoupled from the D/A converter 14 by the capacitor 52. The functions of the crossed diode 53 are to protect the input stage of the preamplifier 6 such that leakage of the high power RF exciting pulse occurs from the transmitter end 30 and the object 20 to the preamplifier 6, and also to prevent distortions caused by the variable capacitance diode 51.

It is obvious that another modifications as shown in FIGS. 5 and 6 may be utilized in another embodiments according to this second technical idea.

The control voltage "$V_R$" to be applied to the variable capacitance diode 51 is produced in the following tuning operation.

As an initial condition, the object 20 such as a patient is positioned within a range defined by the transmitter/receiver probe heads 1 and 2, and the selector switches 40 and 50 are changed to the tuning control mode, i.e., as shown in FIG. 7. Under these conditions, the receiver probe head 2 is being connected to SSG 4 in the transmitter unit 30, and the CW signal is being applied to the receiver probe head 2, which is a low voltage and is not modulated by the modulator 32, and having the resonant frequency.

Figure 9A:
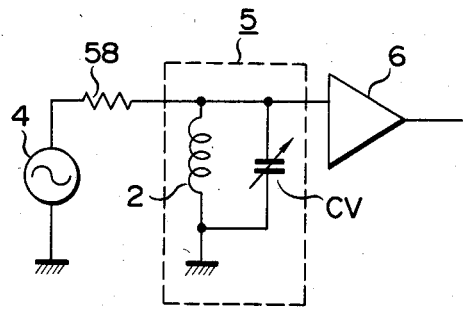
FIGS. 9A and 9B are equivalent circuits for explaining the automatic tuning unit.
Figure 9B:
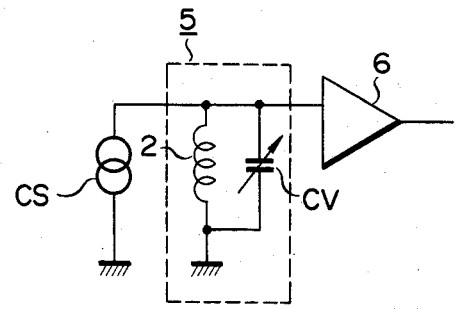

Assuming that the resistor 58 has a great resistance, equivalent circuits of the receiver tuning unit 5 can be represented in FIGS. 9A and 9B. That is, a current source "CS" having the resonant frequency is connected parallel to the parallel resonant circuit consisting of the receiver probe head 2 and a combined capacitance circuit "CV". This combined capacitance circuit "CV" is a combination of the variable capacitance diode 51 and the capacitor 52. A voltage appearing across the parallel resonant circuit is applied to the envelope detector 44 via the preamplifier 6, the switch 40 and the amplifier 42 (see FIG. 7). The envelope detector 44 is constructed by diodes (not shown) and derives envelope components of the input CW signal, i.e., DC components proportional to the amplitude of the input CW signal. The DC components of the detected CW signal are converted by the A/D converter 46 into corresponding digital signals which are supplied to the signal processor 13.

The same as in the previous tuning operation, the output analog voltage from the D/A converter 14, i.e., the control voltage "Vc" when no CW signal is applied to the receiver probe head 2 is set to the minimum voltage "Vo". Then the voltage appearing across the receiver tuning unit 5 when the CW signal is being applied to the receiver probe head 2, is amplified, envelope-detected, A/D-converted, and applied to the signal processor 13. This input digital signal (DC voltage) is temporarily stored in the proper storage means of the signal processor 13. A series of such digital signals is sequentially obtained and compared to each other so as to find out the desirable control voltage "$V_R$" according to the same automatic tuning operation as the descriptions with respect to the embodiments shown in FIGS. 3 and 4.

Thereafter since the automatic tuning operation has been completed, the selector switches 40 and 50 are changed over the mode of the NMR signal acquisition. That is, the contact of the switch 40 is switched to the upper position, and switch 50 is changed to the "OFF" position. Accordingly the receiver probe head 2 and the receiver tuning unit 5 are connected to the NMR signal reception circuit for the tomographic images. In this stage, the optimum control voltage "$V_R$" is being applied to the variable capacitance diode 51, so that the tuning between the receiver probe head 2 and the patient 20 can be realized. The above-mentioned automatic tuning operation is carried out when one patient is substituted by the other patient, and also the diagnostic portion of the patient is changed, so that a tuning of the receiver tuning unit 5 can be automatically realized.

According to the second technical idea, the CW signal for the transmitter is utilized for the control voltage of the automatic tuning operation, that is different from the NMR signal method according to the first technical idea. Consequently it is possible to obtain the optimum tuning voltage "$V_R$" within a short time period.

Further embodiments belonging to the second technical ideal will now be explained.

Figure 10:
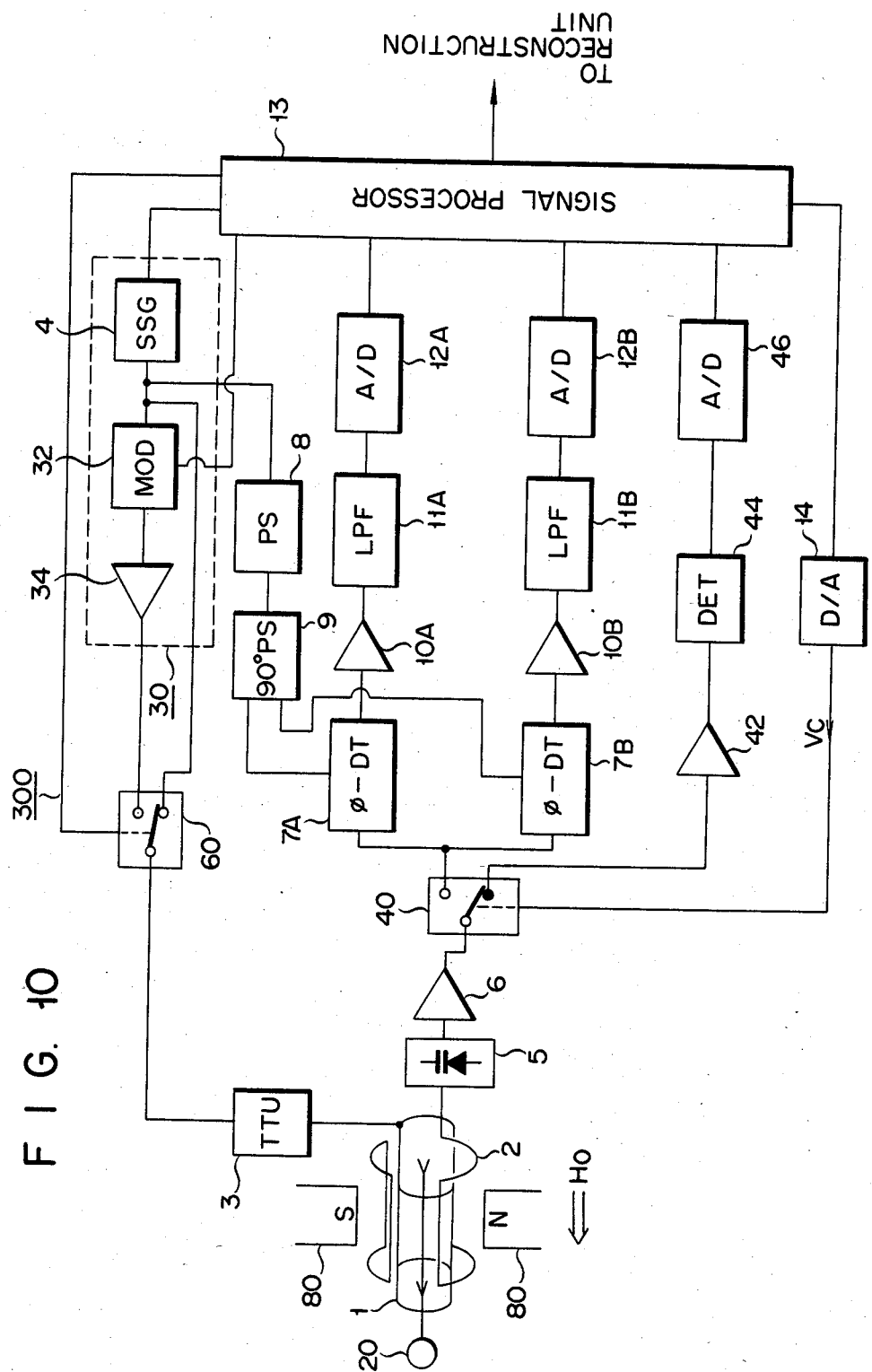
FIG. 10 shows a block diagram of another preferred embodiment belonging to the second technical idea according to the invention.

For example, while the CW signal derived from SSG 4 was applied to the receiver probe head 2 in the previous embodiment, an NMR diagnostic apparatus (300) as shown in FIG. 10 is realized as follows. At first, the CW signal generated from the transmitter unit 30 is applied to the transmitter probe head 1 through a selector switch 60. In this case, this CW signal is not processed in the modulator 32 and the power amplifier 34, but is directly passed through the selector switch 60 which is controlled by the signal processor 13. While the signal is being applied to the transmitter probe head 1, very weak leakage voltage induced by the receiver probe head 2 is amplified, and envelope-detected as explained hereinbefore. Then the similar automatic tuning operation can be realized in this embodiment.

As already explained with reference to the modifications of the first technical idea, the following similar modifications can be also realized in this technical idea.

For instance, another variable capacitance diode 21 may be introduced instead of the capacitor 52 as shown in FIG. 5. A connection direction between the capacitor 52 and the variable capacitance diode 51 may be changed in an opposite sense. A loop type probe head coil can be alternatively employed. Moreover, a single type transmitter/receiver head coil 15 as shown in FIG. 6 may be utilized instead of the crossed coil type one.

Figure 4:
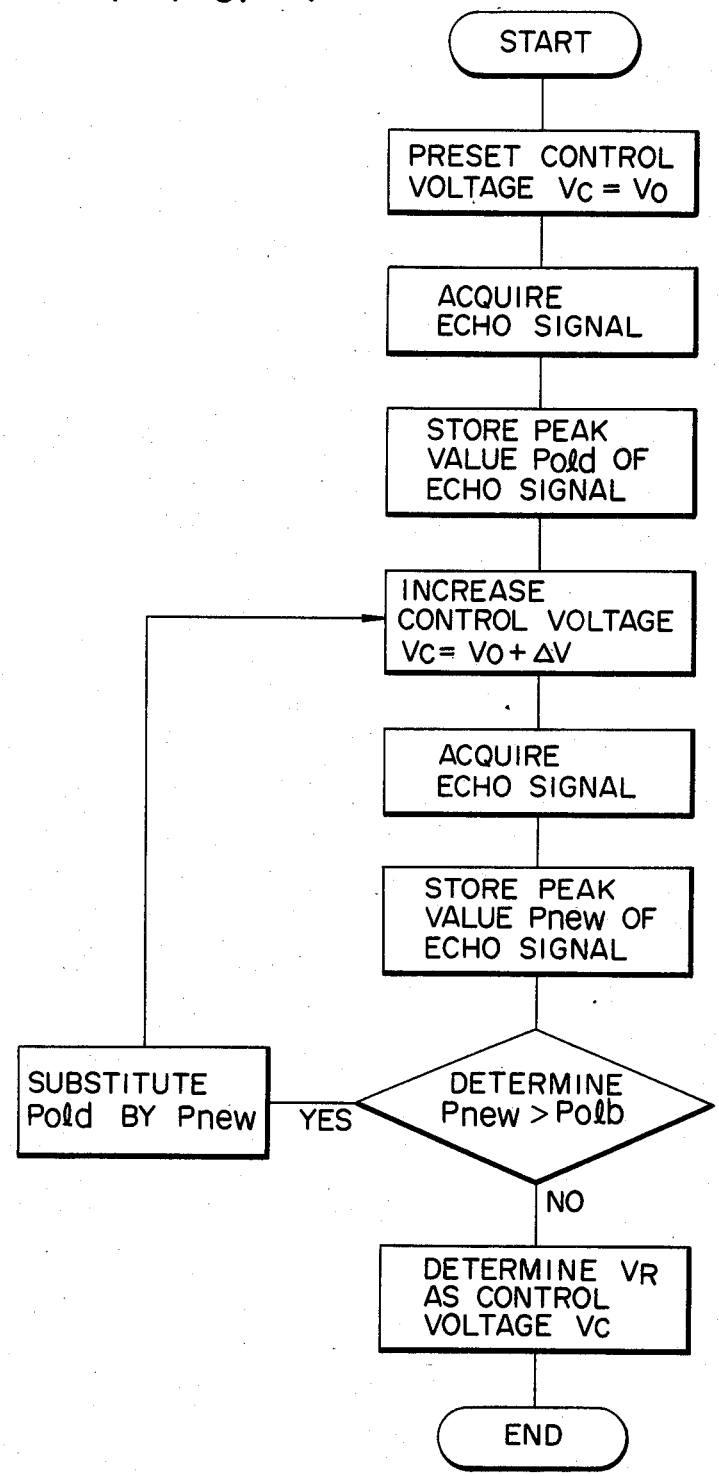
FIG. 4 is a flow chart for operations of the automatic tuning unit.

It should be noted that the sequential operations of the automatic tuning operation which are described with reference to the flow chart shown in FIG. 4 can be modified by changing the program on the control voltage "$V_R$" for the signal processor 13 without departing from the technical spirit and scope according to the present invention.

As previously described in greater detail, the NMR diagnostic apparatus can be provided according to the present invention, in which the receiver tuning unit is automatically brought into the tuning condition within a short time.

What is claimed is:

1. An automatic tuning circuit for an NMR apparatus wherein NMR signals are produced in an object under examination by applying thereto magnetic fields in conjunction with RF pulses, said circuit comprising:

receiving coil means for receiving said NMR signals from said object;

quadrature detector means for quadrature-detecting said NMR signals received by said receiving coil means and for obtaining peak values thereof;

control signal generator means for generating a control signal in response to said peak values of said quadrature-detected NMR signals; and receiver tuning means, including a parallel resonant circuit having a variable capacitance element coupled to said receiving coil means, for automatically controlling said variable capacitance element in response to said control signal to tune said receiver tuning means with respect to said object.

2. An apparatus of claim 1, wherein said NMR signals and said control signal are analog signals and said control signal generator means includes:

an A/D converter which converts said analog NMR signals detected by said quadrature detection means into corresponding digital NMR signals;

signal processor means, connected to said A/D converter, for presetting said control signal to a minimum digital value when no NMR signal is received in said receiving coil means, temporarily storing the peak values of said digital NMR signals, and subsequently generating said control signal at a digital value higher than said minimum value in response to said stored peaked values; and a D/A converter which converts said control signal into a corresponding analog form.

3. An apparatus of claim 1, wherein said receiver tuning means further includes:

a capacitor having a greater capacitance than that of said variable capacitance element and which is series-connected to said variable capacitance element, and whereby a series arrangement of said variable capacitance element and said capacitor is connected parallel to said receiver tuning means to form said parallel resonant circuit.

4. An apparatus of claim 1, wherein said receiver tuning means further includes:

a second variable capacitance element series-connected to said first variable capacitance element with said control signal applied to both said first and second variable capacitance elements.

5. An apparatus of claim 1 further including means for transmitting said RF pulses and wherein:

said transmitter means and said receiving coil means comprise a common coil assembly;

said receiver tuning means further includes a variable capacitor and an auxiliary coil which are series-connected to each other, thereby forming a first series arrangement of said common coil assembly, said variable capacitor, and said auxiliary coil; and said receiver timing means further includes an additional capacitor, having a greater capacitance than that of said variable capacitance element, series-connected to said variable capacitance element, whereby a second series arrangement comprising said variable capacitance element and said additional capacitor is connected parallel to said first series arrangement.

6. An apparatus of claim 3, further comprising:

a crossed diode connected parallel to said parallel resonant circuit; and a resistor interposed between said control signal generator means and the junction of said variable capacitance element and said capacitor.

7. An apparatus of claim 4 further comprising:

a crossed diode connected parallel to said parallel resonant circuit; and a resistor interposed between said control signal generator means and the junction between said first variable capacitance element and said second variable capacitance element.

8. An apparatus as claimed in claim 5, further comprising:

a crossed diode connected parallel to said parallel resonant circuit; and a resistor interposed betrween said control signal generator means and the junction between said variable capacitance element and said additional capacitor.

9. An automatic tuning circuit for an NMR apparatus wherein NMR signals are produced in an object under examination by applying thereto magnetic fields in conjunction with RF pulses that are produced by a continuous wave signal, said circuit comprising:

receiving coil means for selectively receiving either said NMR signals from said object or said continuous wave signal;

envelope detector means for envelope-detecting said continuous wave signal to obtain a DC tuning signal having an amplitude proportional to the amplitude of said continuous wave signal;

coil signal generator means for generating a control signal in response to said DC tuning signal; and receiver tuning means, including a parallel resonant circuit having a variable capacitance element coupled to said receiving coil means, for automatically controlling said variable capacitance element in response to the control signal to tune said receiver tuning means with respect to said object.

10. An apparatus of claim 9, wherein said DC tuning signal and said control signals are analog signals and said control signal generation means includes:

an A/D converter which converts said DC tuning signal into a corresponding digital signal;

signal processor means, connected to said A/D converter, for presetting said control signal to a minimum digital value when no continuous wave signal is received in said receiving coil means, temporarily storing the values of said DC tuning signals, and subsequently generating said control signal at a digital value higher than said minimum value in response to said DC tuning signal; and a D/A converter which converts said control signal into a corresponding analog form.

11. An apparatus of claim 9, wherein said receiver tuning means further includes:

a capacitor having a greater capacitance than that of said variable capacitance element and which is series-connected to said variable capacitance element, and whereby a series arrangement of said variable capacitance element and said capacitor is connected parallel to said receiver tuning means to form said parallel resonant circuit.

12. An apparatus of claim 9, wherein said receiver tuning means further includes:

a second variable capacitance element series-connected to said first variable capacitance element with said control signal applied to both said first and second variable capacitance elements.

13. An apparatus of claim 9 further including means for transmitting said RF pulses and wherein:
   said transmitter means and said receiving coil means comprise a common coil assembly;
   said receiver tuning means further includes a variable capacitor and an auxiliary coil which are series-connected to each other, thereby forming a first series arrangement of said common coil assembly, said variable capacitor, and said auxiliary coil; and
   said receiver tuning means further includes an additional capacitor, having a greater capacitance than that of said variable capacitance element, series-connected to said variable capacitance element, whereby a second series arrangement comprising said variable capacitance element and said additional capacitor is connected parallel to said first series arrangement.

14. An apparatus of claim 11, further comprising:
   a crossed diode connected parallel to said parallel resonant circuit; and
   a resistor interposed between said control signal generator means and the junction of said variable capacitance element and said capacitor.

15. An apparatus of claim 12, further comprising:
   a crossed diode connected parallel to said parallel resonant circuit; and
   a resistor interposed between said control signal generator means and the junction between said first variable capacitance element and said second variable capacitance element.

16. An apparatus of claim 13, further comprising:
   a crossed diode connected parallel to said parallel resonant circuit; and
   a resistor interposed between said control signal generator means and the junction between said variable capacitance element and said additional capacitor.

* * * * *